United States Patent [19]

Blass

[11] Patent Number: 5,527,708
[45] Date of Patent: Jun. 18, 1996

[54] SENSITIVE AND HIGHLY SPECIFIC QUANTITATIVE FLUOROMETRIC ASSAY FOR CREATININE IN BIOLOGICAL FLUIDS

[76] Inventor: Karl G. Blass, P.O. Box 964, Regina, Saskatchewan, Canada, S4P 3B2

[21] Appl. No.: 433,716

[22] Filed: May 2, 1995

Related U.S. Application Data

[63] Continuation-in-part of Ser. No. 161,393, Dec. 6, 1993, abandoned.

[30] Foreign Application Priority Data

Dec. 11, 1992 [GB] United Kingdom .................. 9225935

[51] Int. Cl.$^6$ .................................................. G01N 33/00
[52] U.S. Cl. .................. 436/98; 436/96; 436/106; 436/164; 436/169; 436/172; 422/56; 422/82.08
[58] Field of Search .................................. 436/91, 96, 98, 436/106, 164, 169, 170, 172; 422/56, 82.05, 82.08

[56] References Cited

U.S. PATENT DOCUMENTS

| | | | |
|---|---|---|---|
| 5,008,078 | 4/1991 | Yaginuma et al. | 422/56 |
| 5,286,624 | 2/1994 | Terashima et al. | 422/56 X |

OTHER PUBLICATIONS

Ebbing—General Chemistry, 1984, pp. 494–495.
Benedict et al Journal of Biological Chemistry, vol. 114, 1936, pp. 515–532.
Parekh et al Clinical Chemistry, vol. 23/11, pp. 2066–2071, 1977.
Langley et al Journal of Biological Chemistry, vol. 115, pp. 333–341, 1936.
Parekh et al Clinica Chimica Acta, vol. 73, 1976, pp. 221–231.
Narayanan et al Clinical Chemistry, vol. 26/8, pp. 1119–1126, 1980.

*Primary Examiner*—Jill Warden
*Assistant Examiner*—Marueen M. Wallenhorst
*Attorney, Agent, or Firm*—Adrian D. Battison; Murray E. Thrift

[57] ABSTRACT

A quantitative assay for creatinine has been developed in which creatinine is reacted with 3,5-dinitrobenzoate under alkaline reaction conditions to produce a fluorophore product which has excitation and emission maxima near 410 nm and 475 nm, respectively. Alternatively, 3,5-dinitrobenzoyl chloride or methyl-3,5-dinitrobenzoate may be employed as reagents. The chemical reactions proceed in the presence of Group IA bases and/or quaternary alkyl ammonium hydroxides under aqueous, nonaqueous and mixed solvent conditions. Detection limits for creatinine are well below one micromole per liter. Conversely, the reactivity of creatinine and/or base with 3,5-dinitrobenzoate may be employed to quantify 3,5-dinitrobenzoate by fluorescence intensity measurements. The chemical assay is readily adaptable to reagent pad and dry-layered coating technologies employing fluorescence detection/quantitation.

21 Claims, 1 Drawing Sheet

SENSITIVE AND HIGHLY SPECIFIC QUANTITATIVE FLUOROMETRIC ASSAY FOR CREATININE IN BIOLOGICAL FLUIDS

This is a continuation-in-part of application Ser. No. 08/161,393, filed on Dec. 6, 1993 and now abandoned.

FIELD OF THE INVENTION

The invention relates to a new and useful chemical assay for the quantitative fluorometric measurement of creatinine in biological fluids. Creatinine is reacted with an alkaline 3,5-dinitrobenzoate reagent solution to produce a fluorophore product that exhibits excitation and emission bands with maximum wavelengths near 410 nm and 470 nm, respectively. Alternatively, 3,5-dinitrobenzamide, 3,5-dinitrobenzoyl chloride or methyl-3,5-dinitrobenzoate may be employed as reagents. When the reactants are applied conversely, the aforementioned chemical reaction may be employed to quantify 3,5-dinitrobenzoate.

BACKGROUND OF THE INVENTION

Some background to this invention is shown in the following references:

1. Jaffe', M.: Ueber den Niederschlag welchen Pikrinsaeure in normalen Harn erzeugt und ueber eine neue Reaction des Kreatinins. *Z. Physiol. Chem.* 10, 391–400 (1886).

2. Tanganelli, E., Prencipe, L., Bassi, D., Cambiaghi, S. and Murador, E.: Enzymic assay of creatinine in serum and urine with iminohydrolase and glutamate dehydrogenase. *Clin. Chem.* 28, 1461–1464 (1982).

3. Soldin, S.J. and Hill, G.J.: Micromethod for determination of creatinine in biological fluids by high-performance liquid chromatography combined with a continuous-flow microanalyzer. *Clin. Chem.* 24, 747–750 (1978).

4. Blass, K.G.: Polarographic studies of the reactivity of bilirubin ditaurine conjugate with alkaline picrate. *Microchem. J.* 35, 334–339 (1987).

5. Blass, K.G. and Ng, D.S.K.: Reactivity of acetoacetate with alkaline picrate: An interference of the Jaffe' reaction. *Clin. Biochem.* 21, 39–47 (1988).

6. Viraraghavan, S. and Blass, K.G.: Effect of glucose upon alkaline picrate: A Jaffe' interference. *J. Clin. Chem. Clin. Biochem.* 28, 95–105 (1990).

7. Benedict, S.R. and Behre, J.A.: Some application of a new color reaction for creatinine. *J. Biol. Chem.* 114, 512–532 (1936).

8. Bolliger, A.: the colorimetric determination of creatinine in urine and blood with 3,5-dinitrobenzoic acid. *Med. J. Austr.* 2, 818–821 (1936).

9. Langley, W.D. and Evans M.: The determination of creatinine with sodium 3,5-dinitrobenzoate. *J. Biol. Chem.* 115, 333–341 (1936).

10. Parekh, A.C., Cook, S., Sims, C., and Jung, D.H.: A new method for the determination of serum creatinine based on reaction with 3,5-dinitrobenoyl chloride in an organic medium. *Clin. Chim. Acta* 73, 221–231 (1976).

11. Sims, C. and Parekh, A.C.: Determination of serum creatinine by reaction with methyl-3,5-dinitrobenzoate in methyl sulfoxide. *Ann. clin. Biochem.* 14, 227–232 (1977).

12. Blass, K.G., Thibert, R.J. and Lam, L.K,: A study of the mechanism of the Jaffe' reaction. *Z. Klin. Chem. Klin. Biochem.* 12, 336–343 (1974).

13. Ng, D.S.K. and Blass, K.G.: Reactivity of Hydroxide ion with picrate as related to the Jaffe' reaction. *Microchem. J.* 36, 89–97 (1987).

Laboratory methods employed for the determination of creatinine in body fluids may be summarized as procedures based upon the Jaffe' reaction (1), coupled enzymatic reactions (2), and high-performance liquid chromatography (HPLC) (3). These methods have varying degrees of specificity (4–6) with the simplest economical procedures being based upon the alkaline picrate Jaffe' reaction which was first published in 1886. Dependent upon the modifications introduced, specificity has been improved, however no routine modified Jaffe' method is free of interference. More costly coupled enzymatic methods have been developed, however these are not in widespread use. While HPLC methods are highly specific and even being considered as reference methods, they are not practical for routine high-volume testing purposes.

The reactivity of creatinine with alkaline 3,5-dinitrobenzoate to produce a purple colored product was first described in the literature in 1936 (7–9). The colorimetric reaction has subsequently been praised for its specificity, but also criticized for its lack of sensitivity. Further improvements have been claimed by employing 3,5-dinitrobenzoyl chloride (10) or methyl-3,5-dinitrobenzoate (11) as reagents for the colorimetric determination of creatinine.

SUMMARY OF THE INVENTION

In contrast, the present studies have discovered an intense fluorescent product which forms when creatinine is reacted with alkaline 3,5-dinitrobenzoate solution. The resulting chemical reaction is both sensitive and highly specific for the quantitative analysis of creatinine. Similar fluorescent product formation has also been observed with 3,5-dinitrobenzoyl chloride or methyl-3-,5-dinitrobenzoate as reagents for the determination of creatinine. The chemical reaction between creatinine and aqueous alkaline picrate, commonly known as the Jaffe' reaction, produces a red 1:1 creatinine product of known structure (12). By way of comparison, the chemical reaction between creatinine and aqueous alkaline 3,5-dinitrobenzoate products a purple colored product. Based upon reaction similarities with additional polarographic and spectrophotometric analyses, the following structure may be assigned to the purple product (FIG. 1). Major features include, the attack of the methylene group of creatinine onto the para position of 3,5-dinitrobenzoate, with one of the nitro groups being transformed into a nitro anion. Dependent upon solution conditions, i.e. pH, temperature, dissolved gases, and reagent concentrations, the negative charge on the nitro group may delocalize with time.

The purple product of the colorimetric reaction was observed to fade with time, subsequently producing a new fluorescent product. By modifying the reaction conditions, i.e. pH, temperature, and reagent concentrations, minimal purple color was observed to form while fluorescence development was greatly enhanced. In the presence of excess hydroxide ions, the purple colored product is rapidly transformed into a colorless product. To further account for minimal color development, hydroxide ions may react with 3,5-dinitrobenzoate to form hydroxide-3,5-dinitrobenzoate products which in turn react with creatinine. Similar hydroxide-picrate products have previously been described (13). The fluorescent product is likely a 1:1:1 hydroxide-3,5-dinitrobenzoate-creatinine. In any event, the fluorescent product has not previously been described and is distinctly different from the purple colored product reported in the chemical literature.

Common Jaffe' reaction interferences like acetone, glucose, pyruvate and the like have been tested with the new procedure and found not to fluoresce. The chemical process described herein is both sensitive and highly specific for the quantitative measurement of creatinine in plasma, serum, spinal fluid, amniotic fluid and urine. The procedure may similarly be employed to quantify creatinine in other fluids, tissues or solids brought into solution. The process, with or without modification may be adapted to commercial fluorometers or fluorometric instrumentation may be specifically designed for this purpose. The process would readily lend itself to dry-layered coating technology.

In the present invention the creatinine present in biological materials is reacted with alkaline 3,5-dinitrobenzoate in aqueous, nonaqueous or mixed solvent to produce a fluorescent product. The chemical reaction readily proceeds at room temperature, however the temperature may be increased or decreased to accelerate or decelerate the rate of the reaction. The maximum excitation and emission wavelengths are near 410 nm and 470 nm, respectively. The excitation full bandpass varies from approximately +/−30 nm to +/−45 nm. The emission full bandpass varies from approximately +/−75 nm to +/−85 nm.

The fluorescence intensity of the test solution is proportional to the creatinine concentration present with a detection limit being well below 1 umol/L. End-point, multiple-point or kinetic method may be employed to quantify creatinine. Alternatively, 3,5-dinitro-benzoyl chloride, 3,5-dinitro-benzamide or methyl-3-,5-dinitrobenzoate may be employed as reagents. Conversely, the reactivity of creatinine and/or base with 3,5-dinitrobenzoate may also be employed to quantify 3,5-dinitrobenzoate by fluorescence measurements.

In order to obtain the reaction of the present invention the excess base concentration must be maintained to a sufficiently high level greater than that of the prior art and preferably greater than 0.31 M as set out hereinafter in Table II. Approximate molar concentrations may be calculated by dividing each of the values in Table II by a factor of 1.6. As the concentration of lithium hydroxide is increased, the fluorescence intensity increases to a maximum and declines thereafter. This is a general characteristic that tends to vary for each of the alkali tested and the solvents and solvent mixtures employed. The decline in fluorescence intensity is attributed to the conversion of the fluorophore product to a nonfluorescent product. Up till now however none of the researchers in the scientific literature has found a fluorescent creatinine product and its possibility for the detection of the amounts of a compound.

Dimethylsulfoxide is a particularly useful solvent for the present study. Dimethylsulfoxide mixes readily with water, increases solubility of the dinitrobenzoates (especially methyl-3,5-dinitrobenzoate) and immensely enhances fluorophore product formation.

DETAILED DESCRIPTION

Figure 1:
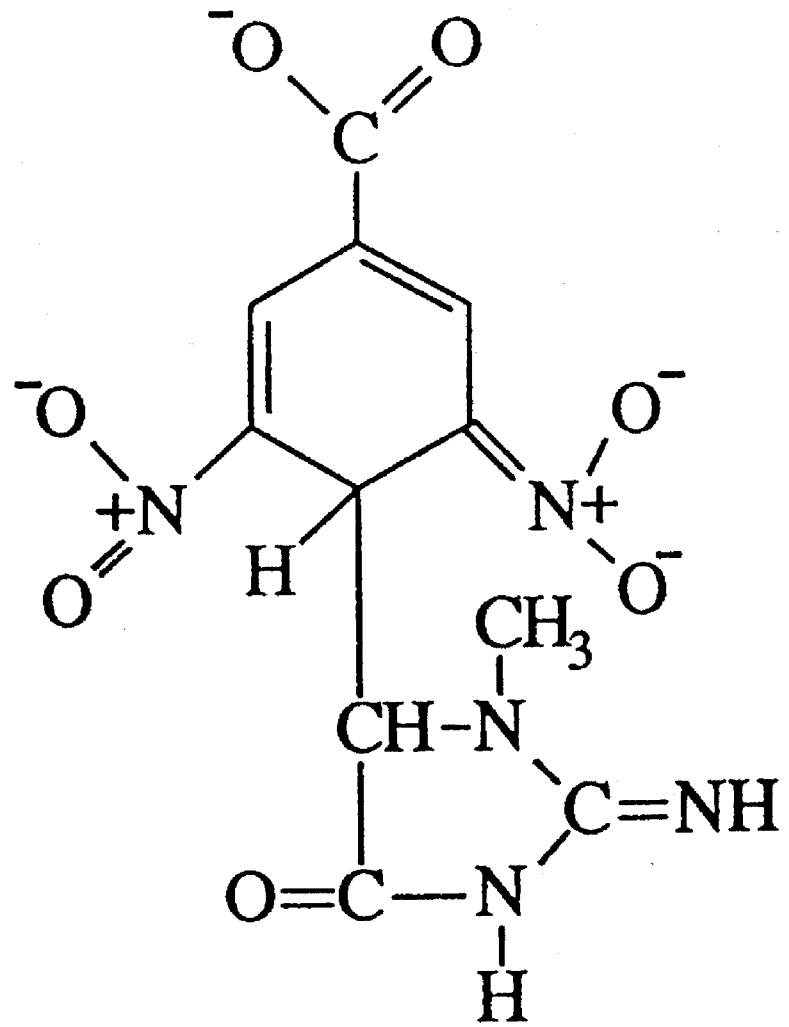
FIG. 1 is an illustration of the prior art structure of the Purple product produced in the prior art process.

The detailed process described herein is presented by way of example only.

All chemicals employed were of reagent grade quality.

Excitation and emission spectra were recorded on a Farrand Mark I Spectrofluorometer equipped with a xenon arc stabilizer (Farrand Optical Company, Inc., Mount Vernon, N.Y.). The fluorescence intensity was recorded on a Farrand Model 100 strip-chart recorder (Model SR-204, Heath Company, Benton Harbor, Mich.). Sample and reagent were added with a Gilford Automatic Pipetter/Diluter (Gilford Instrument Laboratories Inc., Mississauga Ontario, Canada).

Detection Limit and Calibration Curve

A creatinine stock solution of 1.0 mmol/L was prepared in distilled water. A creatinine working solution was prepared by adding 1.0 mL of stock solution to a 100 mL volumetric flask which was filled to volume with distilled water and mixed by inversion. A Gilford Automatic Pipetter/Diluter was employed to add creatinine working solution.

A 0.5303 g weight of 3,5-dinitrobenzoic acid (DNB) was added to a 50-mL volumetric flask containing approximately 45 mL of 2,4-butanediol (BTD). To facilitate dissolution of the dinitrobenzoic acid, the flask was mixed by agitation on a Nutator mixer (Becton, Dickinson and Company Canada Ltd., Mississauga, Ontario, Canada). The flask was brought to volume with 2,4-butanediol and mixed by inversion.

A 1.0 mL volume of DNB-BTD solution was added to a quartz cuvet. A Gilford Automatic Pipetter/Diluter was employed to add to the cuvet 1.0 mL of 1.0 M NaOH and 0.1 mL of creatinine working solution. For subsequent test solutions the volume of creatinine working solution was decreased to 50%, 40%, 20% and finally to 10%. Each of the test solutions described above as similarly performed in duplicate. The detection limit for creatinine was below 1 umol/L.

A calibration curve was similarly performed as described above for concentrations of 5,10,20,30,40 and 50 umol/L. Each of the test concentrations was similarly reproduced in duplicate. The results have been tabulated in Table 1.

Effect of Lithium Hydroxide Concentration upon Fluorescence Development

Aliquots of an aqueous 2.5 M lithium hydroxide solution were diluted to produce base concentrations of approximately 0.5,0.7, 0.95, 1.25, 1.56, 1.8 and 2.1 molar. A freshly saturated solution of 3,-5-dinitrobenzoic acid was prepared in isopropanol. An aliquot was removed and diluted with an equal volume of isopropanol. A blank solution was prepared by adding 1.0 mL of 0.5 M lithium hydroxide to a cuvet. A Gilford Automatic Pipetter/Diluter was employed to add 0.5 mL of 3,5-dinitrobenzoic acid working solution to the cuvet. The blank solution was mixed ten times by inversion. The fluorescence intensity was monitored for 10 minutes employing a Farrand Mark I Spectrofluorometer. Excitation and emission wavelengths were 410 and 476 nm, respectively. Blanks were similarly prepared and tested for each of the lithium hydroxide concentrations up to and including 2.5 M. Test solutions were similarly prepared with the Gilford Pipetter/Diluter adding 0.1 mL of a 1.0 mmol/L creatinine stock solution to each cuvet. The concentration of alkali in the total reaction solution after mixture for the lowest concentration of 0.5 M is this value divided by 1.6 which provides a resultant concentration of approximately 0.31 M.

Test solutions for each of the base concentrations were similarly prepared and fluorescence intensity was monitored for up to 5 minutes. The change in fluorescence intensity with time was calculated between 1 and 2 minutes and the data has been tabulated in Table II. The fluorescence intensity of each of the blank solutions was stable for over 10 minutes.

Aqueous Combined Reagent for the Determination of Creatinine

A combined aqueous reagent was prepared by mixing 20 milliliters of 1.0 M lithium hydroxide with 20 milliliters of a 30 mmol/L 3,5-dinitrobenzoate solution. The reagent was dispensed with a Gilford Dispenser/Diluter directly into a cuvet. Creatinine concentrations were varied between 0.01 mL and 0.08 mL in increments of 0.01 mL. Test solutions were mixed ten times by inversion. The development of fluorescence was monitored for five minutes with a Farrand Mark I Spectrofluorometer. Excitation and emission wavelengths were 406.5 nm and 476 nm, respectively. The results have been tabulated in Table III.

Reagent Pad and Dry-Layered Coating Technology

Filter paper is dipped into a solution containing 3,5-dinitrobenzoate salt. The solvent is evaporated leaving a 3,5-dinitrobenzoate salt residue both on the surface and within the pores of the filter paper. Other inert support matrices like quartz, ground quartz, cellulose, silica gel, silicic acid, glass or glass fibers and the like may of course be substituted. The addition of ten or twenty microliters of alkaline fluid containing small quantities of creatinine results in dissolution of the 3,5-dinitrobenzoate and subsequent fluorophore product development. By way of example the base concentration may be 1 molar with the creatinine concentration being 100 to 500 micromolar. Formation of the fluorophore is monitored by reflectance fluorometry. By way of another example, both the 3,5-dinitrobenzoate salt and lithium hydroxide may be layered onto an inert support matrix. The addition of aqueous solution containing low levels of creatinine results in dissolution of the reagents with some localized heat being generated by the solvation of the lithium hydroxide. This approach provides additional energy and accelerates the chemical reaction. Conversely, the procedure may of course be inverted, wherein excess alkaline creatinine is localized upon or within an inert matrix, with a dilute solution of 3,5-dinitrobenzoate being added to the reagent strip. The latter procedure would be employed to quantitate 3,5-dinitrobenzoate.

For the purpose of measurement of the fluorescence a fluorometer of conventional type well known to one skilled in the art is used and this is used with monochromators and/or bandpass filters which are used to permit the passage of light near 410 nm for excitation and cut-off filters which are used to permit light near 455 nm or 475 nm to pass through for detection. The arrangement of both monochromators and filters will be well known to one skilled in the art.

Methyl-3,5-dinitrobenzoate in Dimethylsulfoxide

Methyl-3,5-dinitrobenzoate was not very soluble in distilled water. Crystals of methyl-3,5-dinitrobenzoate were dissolved in dimethylsulfoxide just prior to testing. A 1.0 mL volume containing methyl-3,5-dinitrobenzoate in dimethylsulfoxide was pipeted into a quartz cell. A 1.0 mL volume of 1.0 M sodium hydroxide was added, immediately followed by 0.1 mL of aqueous creatinine with mixing by inversion five times. Alternatively, volumes of plasma, serum or diluted urine have been substituted. The excitation and emission wavelengths were 410 nm and 455 nm, respectively. A very rapid reaction took place that covered three ranges of the fluorometer scale. The cuvet was warm, indicating that the reaction was heat accelerated. To evaluate the chemical heat production, a 1.0 mL volume of dimethylsulfoxide was mixed with 1.0 mL of 1.0 M sodium hydroxide in a cuvet. The temperature was observed to rise from 24 to 36 degrees Celsius.

TABLE I

Reactivity of Creatinine with Alkaline 3,5-Dinitrobenzoate in Aqueous 1,4-Butanediol*

| Creatinine umol/L | Microamperes** |
| --- | --- |
| 0 | 12.1 |
| 5 | 20.8 |
| 10 | 30.4 |
| 20 | 48.3 |
| 30 | 65.9 |
| 40 | 82.5 |
| 50 | 96.3 |

*Spectrofluorometer excitation and emission wavelenths were 410 nm and 475 nm, respectively.
**Each result reported represents an average of two test analyses. Refer to text for complete details.
The current value as measured on the Spectrofluorometer is measured in microamps $\times 0.3 \times 10^{-3}$.

TABLE II

Effect of Lithium Hydroxide Concentration Upon the Reactivity of Creatinine with 3,5-Dinitrobenzoate*

| LiOH concentration** Moles/Liter | Change in Microamperes between 1 and 2 minutes for 1 mmol/Liter creatinine |
| --- | --- |
| 0.50 | 2.4 |
| 0.69 | 5.6 |
| 0.96 | 13.9 |
| 1.25 | 13.3 |
| 1.56 | 22.7 |
| 1.79 | 35.7 |
| 2.08 | 54.3 |
| 2.5 | 32.5 |

*Spectrofluorometer excitation and emission wavelengths were 406.5 nm and 475 nm, respectively.
**A one milliliter volume of each of the lithium hydroxide base concentrations listed was employed. Refer to text for complete details.
The current value as measured on the Spectrofluorometer is measured in micramps $\times 10^{-3}$.

TABLE III

Reactivity of Creatinine with Alkaline 3,5-Dinitrobenzoate in Aqueous Media*

| Creatinine umol/L | Microamperes** |
| --- | --- |
| 100 | 6.9 |
| 200 | 19 |
| 300 | 36 |
| 400 | 56 |
| 500 | 77 |
| 600 | 95 |
| 700 | 115 |
| 800 | 130 |

*Spectrofluorometer excitation and emission wavelengths were 406.5 nm and 475 nm, respectively.
**Each result reported represents an average of two test analyses. Refer to text for complete details.
The current value as measured on the Spectrofluorometer is measured in microamps $\times 0.3 \times 10^{-3}$.

I claim:

1. A method for detecting an unknown quantity of one of a first compound consisting of creatinine and a second compound consisting of methyl-3,5-dinitrobenzoate, 3,5-dinitrobenzamide or 3,5-dinitrobenzoate in a reaction solution, the method comprising: providing one of the first or second compounds in an unknown quantity; providing said other of said first and second compounds in a known quantity; reacting, under alkaline conditions, said first and second compounds to form a reaction solution; the alkaline conditions being sufficient to produce from the reaction a product that fluoresces; providing a fluorometer and detecting the unknown quantity of said one of the first and second compounds by measuring the fluorescence intensity of the product using the fluorometer.

2. A method according to claim 1 wherein the alkaline conditions are produced by an alkali or mixture of alkali in an amount such that the concentration of the alkali in the reaction solution is greater than 0.31 M.

3. A method according to claim 1 wherein a maximum excitation wavelength of the fluorescent product lies in a band near 410 nm and an emission wavelength of the fluorescent product lies in a band near 455 nm or 475 nm.

4. A method according to claim 1 wherein the first and second compounds are dissolved in a solvent or solvent mixture selected from the group consisting of water, ethanol, isopropanol, 2,4-butanediol, dimethylformamide, and dimethylsulfoxide.

5. A method according to claim 1 wherein the unknown quantity of the first or second compound is detected in a biological solution which is selected from the group consisting of plasma, serum, spinal fluid, amniotic fluid and urine.

6. A method according to claim 1 including providing the fluorometer with bandpass filters which permit the passage of light in a band near 410 nm.

7. A method according to claim 1 including providing the fluorometer with cut off filters which permit light in a band near 455nm or 475 nm to pass through and be detected.

8. A method for detecting an unknown quantity of a first compound consisting of 3,5-dinitrobenzoate in a reaction solution with a second compound comprising an alkali or an alkali and creatinine, the method comprising: providing an unknown quantity of the first compound; providing a known quantity of the second compound; reacting said unknown quantity of the first compound with the known quantity of the second compound under alkaline conditions to form a reaction solution the alkaline conditions being sufficient to produce from the reaction a product that fluoresces; providing a fluorometer and detecting the unknown quantity of said first compound by measuring the fluorescence intensity of the product with the fluorometer.

9. A method according to claim 8 wherein the alkaline conditions are produced by an alkali or mixture of alkali in an amount such that the concentration of the alkali in the reaction solution is greater than 0.31 M.

10. A method according to claim 8 wherein a maximum excitation wavelength of the fluorescent product lies in a band near 410 nm and an emission wavelength of the fluorescent product lies in a band near 455 nm or 475 nm.

11. A method according to claim 8 wherein the alkaline conditions are mainly provided by an alkali selected from the group consisting of lithium hydroxide, sodium hydroxide, potassium hydroxide, rubidium hydroxide, cesium hydroxide, and mixtures thereof.

12. A method according to claim 8 including providing the fluorometer with bandpass filters which permit the passage of light in a band near 410 nm.

13. A method according to claim 8 including providing the fluorometer with cut off filters which permit light in a band near 455 nm or 475 nm to pass through and be detected.

14. A method for detecting an unknown quantity of a first compound consisting of creatinine in a reaction solution with a second compound, the method comprising: providing an unknown quantity of the first compound; providing said second compound in a known quantity, said second compound selected from the group consisting of 3,5-dinitrobenzoic acid, 3,5-dinitrobenzoyl chloride, 3,5-dinitrobenzoate salt, 3,5-dinitrobenzamide and methyl-3,5-dinitrobenzoate; reacting, under alkaline conditions, said first and second compounds to form a reaction solution; the alkaline conditions being sufficient to produce from the reaction a product that fluoresces; providing a fluorometer; and detecting the unknown quantity of said first compound by measuring the fluorescence intensity of the product using the fluorometer.

15. A method according to claim 14 wherein the alkali conditions are produced by an alkali or mixture of alkali in an amount such that the concentration of the alkali in the reaction solution is greater than 0.31 M.

16. A method according to claim 14 wherein a maximum excitation wavelength of the fluorescent product lies in a band near 410 nm and an emission wavelength of the fluorescent product lies in a band near 455 nm or 475 nm.

17. A method according to claim 14 wherein the first and second compounds are dissolved in a solvent or solvent mixture selected from the group consisting of water, ethanol, isopropanol, 2,4-butanediol, dimethylformamide, and dimethylsulfoxide.

18. A method according to claim 14 wherein the alkaline conditions are mainly provided by an alkali selected from the group consisting of lithium hydroxide, sodium hydroxide, potassium hydroxide, rubidium hydroxide, cesium hydroxide, and mixtures thereof.

19. A method according to claim 14 including providing the fluorometer with bandpass filters which permit the passage of light in a band near 410 nm.

20. A method according to claim 14 including providing the fluorometer with cut off filters which permit light in a band near 455 nm or 475 nm to pass through and be detected.

21. A method according to claim 14 wherein said first and second compounds are dry layers of reagents or impregnated within a dry reagent pad.

* * * * *